US006297404B1

(12) United States Patent
Klatt et al.

(10) Patent No.: US 6,297,404 B1
(45) Date of Patent: Oct. 2, 2001

(54) PROCESS FOR PREPARING OXOISOPHORONE USING ADDITIVES

(75) Inventors: Martin Jochen Klatt, Bad Dürkheim; Thomas Müller, Dirmstein; Bernhard Bockstiegel, Römerberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/598,245

(22) Filed: Jun. 21, 2000

(30) Foreign Application Priority Data

Jun. 25, 1999 (DE) .............................. 199 29 362

(51) Int. Cl.$^7$ ................................................ C07C 45/32
(52) U.S. Cl. .................... 568/320; 568/344; 568/377; 568/378
(58) Field of Search ................................... 568/320, 312, 568/341, 344, 377, 378

(56) References Cited

U.S. PATENT DOCUMENTS 4,026,947  5/1977  Costantini et al. ............... 260/586
5,874,632 * 2/1999  Hahn et al. .

FOREIGN PATENT DOCUMENTS 26 10 254   9/1976  (DE) .
808 816    11/1997  (EP) .
1090 150    4/1989  (JP) .

* cited by examiner

Primary Examiner—Johann Richter
Assistant Examiner—Sikarl A. Witherspoon
(74) Attorney, Agent, or Firm—Keil & Weinkauf

(57) ABSTRACT

The present invention relates to a process for preparing 3,5,5-trimethylcyclohex-2-ene-1,4-dione (oxoisophorone; OIP) by oxidation of 3,5,5-trimethylcyclohex-3-en-1-one (β-isophorone, β-IP) with molecular oxygen in the presence of a solvent, of a base and of a transition metal salen derivative as catalyst and of an additive.

9 Claims, 1 Drawing Sheet

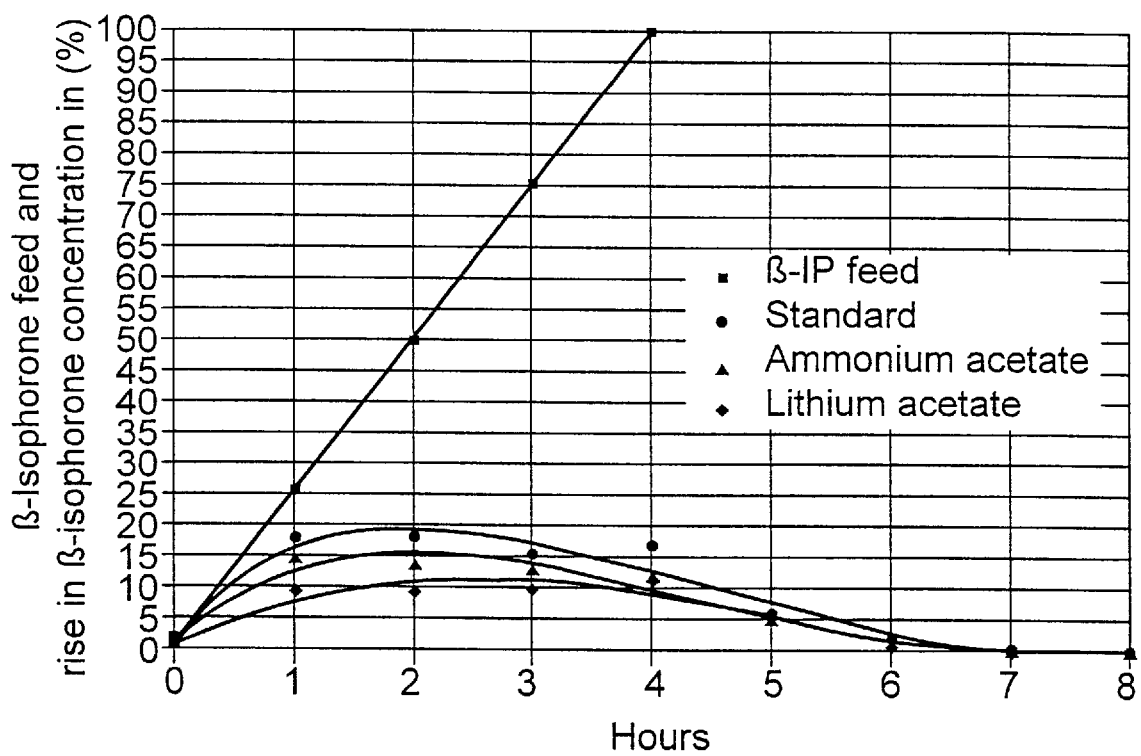

PROCESS FOR PREPARING OXOISOPHORONE USING ADDITIVES

The present invention relates to a process for preparing 3,5,5-trimethylcyclohex-2-ene-1,4-dione (oxoisophorone; OIP) by oxidation of 3,5,5-trimethylcyclohex-3-en-1-one ((β-isophorone, β-IP) with molecular oxygen in the presence of a solvent, of a base and of a transition metal salen derivative as catalyst.

Oxoisophorone (OIP) can be used as flavoring or fragrance in foodstuffs or in cosmetic formulations. OIP is moreover an intermediate for the preparation of vitamins and carotenoids.

It is known to prepare OIP by oxidation of β-isophorone (β-IP) with molecular oxygen in the presence of an inert solvent, of a base and of an Mn or Co salen derivative. DE Patent 2610254 C2 describes the use of a large number of cobalt(II) and manganese(II) salen derivatives as catalysts, it being possible to prepare the salen-like chelate ligands from a number of diamines and hydroxy carbonyl compounds. The list of hydroxy carbonyl compounds mentions, besides many others, also halogenated 2-hydroxybenzaldehydes with a widely variable substitution pattern. The conversions, yields and selectivities achieved in this process are often only low, especially on use of unsubstituted aromatic Mn and Co salens (ligands prepared from various diamines and 2-hydroxybenzaldehyde). Substitution on the aromatic system with electron-attracting radicals, such as introduction of a nitro group, leads, as shown in Example 5 loc. cit., to a lower yield.

JP 01090150 describes aromatic mangangese(III) salen derivatives with a wide variability in the substitution pattern, the substituents, the counter ion and the number of C atoms in the amine bridge as catalysts in an analogous process. The best result is achieved on use of a chlorinated Mn(III) salen with X=acetate as counter ion and with low precursor concentrations, the yields being up to 90.7%. However, the low precursor concentrations mean that the space-time yield is likewise low.

EP 0808816 A1 describes an improved process with addition of catalytic additives such as organic acids, aliphatic alcohols, compounds able to form an enol structure, and lithium sulfate. This is said to achieve good selectivities and thus higher space-time yields even with higher precursor concentrations. Starting from precursor concentrations of 1.4 mol/l, selectivities of up to 92% (acetylacetone) with 80% conversion are achieved by the additions. Acetic acid as additive results in the highest reaction rate ($5.3 \times 10^{-2}$ 1/min). The process has the disadvantage that the space-time yields achieved are possible only on the laboratory scale because on the industrial scale it is not possible in exothermic reactions with molecular oxygen to have large precursor tonnages present initially; on the contrary, they must be introduced slowly (up to 4 hours) into the reaction mixture in order to avoid the risk of explosion. In addition, only 80% conversion means that elaborate removal of the unreacted precursors is necessary.

In all the prior art processes there is formation not only of high boilers, which interfere little with the purification, but also of the following identified byproducts IV (α-isophorone), V, VI and VII, which impede purification or a further chemical reaction of OIP:

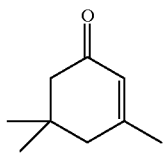

IV

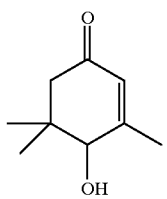

V

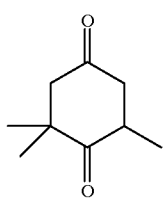

VI

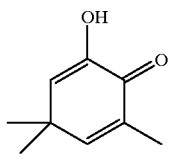

VII

α-Isophorone (IV) is formed in the prior art processes in a yield of up to 3.2%, and compound V is formed in a yield of up to 4.4%. Compound VI particularly interferes with subsequent syntheses because it shows a similar chemical behavior to the product OIP.

Besides the low yields with increasing precursor concentration, another disadvantage common to all the prior art processes is that even under simulated industrial conditions in relation to temperature and oxygen consumption the progress of the reaction is irregular so that large variations during the reaction must be monitored and compensated.

Moreover all the known processes use, from the large number of possible combinations of bases and solvents, triethylamine as base, often combined with diglyme (dimethyldiglycol) as solvent. Since this mixture has an ignition point of 0° C., the known processes can be carried out on the industrial scale only with great safety precautions for this reason too.

Moreover the reaction in the known processes is slow to start so that initially the concentration of the continuously introduced precursor (β-IP) rises. This results in the disadvantage, especially on the industrial scale, that for safety reasons initially a smaller amount of precursor can be introduced, resulting in a lower space-time yield. In addition, an increased proportion of β-isophorone leads to an increased isomerization back to α-isophorone, resulting in a lower selectivity for β-isophorone.

It is an object of the present invention to remedy the disadvantages described and to develop a process which provides good yields, selectivities and space-time yields even with high precursor concentrations also on the industrial scale. It is further intended to reduce the formation of the byproducts IV, V, VI and VII and the rise in the β-IP concentration before the start of the reaction.

We have found that this object is achieved by a process in which 3,5,5-trimethylcyclohex-2-ene-1,4-dione is prepared by oxidation of 3,5,5-trimethylcyclohex-3-en-1-one with molecular oxygen in the presence of a solvent, of a base and of a catalyst of the formula I

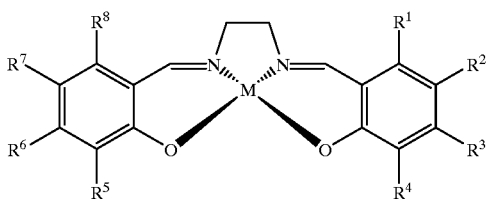

where
$R^1, R^2, R^3, R^4, R^5, R^6, R^7$ and $R^8$ are, independently of one another, hydrogen, halogen, $NO_2$, $COR^9$, $OCOR^9$, $COOR^9$, $SO_2R^9$ or $SO_3R^9$, where
$R^9$ is hydrogen or a $C_1$–$C_4$-alkyl radical,
M is Mn(II), Mn(III)$^{(+)}X^{(-)}$, Co(II), Co(III)$^{(+)}X^{(-)}$, Fe(II), Fe(III)$^{(+)}X^{(-)}$, Cu(II) or Ru(II), where
$X^{(-)}$ is a negatively charged counter ion for metals in oxidation state III,
which process is carried out in the presence of one or more acetate salts of the general formula II $$(R^{10}R^{11}R^{12}C-COO^{(-)})_m Y^{(m+)} \quad (II)$$

as additive, where
$R^{10}, R^{11}$ and $R^{12}$ are, independently of one another, hydrogen, F, Cl, Br, I or a $C_1$–$C_4$-alkyl radical,
Y is $NH_4^+$ or a singly to quadruply charged metal cation and m is 1, 2, 3 or 4.

The starting compound for the process is 3,5,5-trimethylcyclohex-3-en-1-one (β-isophorone; β-IP). Conversion to 3,5,5-trimethyl-cyclohex-2-ene-1,4-dione (oxoisophorone; OIP) takes place in a solvent by oxidation with molecular oxygen in the presence of a base, the aforementioned catalyst of the formula I and acetate salts of the general formula II as additives.

The catalysts of the formula I are metal salen complexes or metal salen derivatives derived therefrom, which consist of a central metal atom and a tetradentate chelate ligand (salen ligand). The salen ligand can be prepared in a manner known per se from ethylenediamine and the appropriate salicylaldehydes which are optionally substituted by $R^1$ to $R^8$.

M means the metals Mn, Co, Fe, Cu or Ru in oxidation state II or III. For equalization of charges, the metals in oxidation state III carry a negatively charged counter ion $X^{(-)}$ in the complex. Examples of negatively charged counter ions $X^{(-)}$ which may be mentioned are halides such as $Cl^{(-)}$, $Br^{(-)}$, $I^{(-)}$, $C_1$–$C_5$ alkanoates such as acetate, propionate or other anions such as $N_3^{(-)}$, thiocyanate, cyanate, isothiocyanate, $BF_4^{(-)}$, $PF_6^{(-)}$, $SO_4^{2(-)}$, $PO_4^{3(-)}$ or $NO_3^{(-)}$. Preferred metals or metals with counter ion are Co(II), Mn(II), or Mn(III)Cl$^{(-)}$.

The aromatic radical in the salen ligand may have no substituents ($R^1=R^2=R^3=R^4=R^5=R^6=R^7=R^8$=hydrogen) or be substituted by the radicals $R^1$ to $R^8$ independently of one another by halogen such as F, Cl, Br or I or $NO_2$, $COR^9$, $OCOR^9$, $COOR^9$, $SO_2R^9$ or $SO_3R^9$. $R^9$ can be hydrogen or a $C_1$–$C_4$-alkyl radical such as methyl, ethyl, n-propyl, i-propyl, n-butyl, i-butyl or t-butyl.

$R^1, R^3, R^6$ and $R^8$ in preferred salen ligands are hydrogen, while the radicals $R^2$ and $R^7$ are the aforementioned substituents, and $R^4$ and $R^5$ are hydrogen or the aforementioned substituents. Particularly preferred salen ligands have $R^1=R^3=R^6=R^8$=hydrogen, $R^2=R^7$=Cl and $R^4=R^5$=hydrogen or Cl.

Accordingly, preferred catalysts are metal salens with Co(II), Mn(II) or Mn(III)Cl$^{(-)}$ as central metal or metal with counter ion and salen ligands with $R^1=R^3=R^6=R^8$=hydrogen, $R^2=R^7$=halogen, $NO_2$, $COR^9$, $OCOR^9$, $COOR^9$, $SO_2R^9$ or $SO_3R^9$ and $R^4=R^5$=hydrogen or halogen, $NO_2$, $COR^9$, $OCOR^9$, $COOR^9$, $SO_2R^9$ or $SO_3R^9$. Particularly preferred metal salens have Mn(II) or Mn(III)Cl$^{(-)}$ as central metal or metal with counter ion and salen ligands with $R^1=R^3=R^6=R^8$=hydrogen, $R^2=R^7$=Cl and $R^4=R^5$=hydrogen or Cl.

The process is carried out in the presence of one or more acetate salts of the general formula II as additive. More than one acetate salt means a mixture comprising two or three acetate salts. The radicals $R^{10}$, $R^{11}$ and $R^{12}$ can moreover be, independently of one another, hydrogen, F, Cl, Br, I or a $C_1$–$C_4$-alkyl radical, as mentioned above for $R^9$.

Y is a positively charged counter ion such as $NH_4^+$ or a metal cation of the 1st–4th main group, such as $Li^+$, $Na^+$, $K^+$, $Ca^{2+}$, or $Mg^{2+}$. The parameter m in the acetate salt represents the acetate coefficient corresponding to the number of positive charges on the counter ion and can be 1, 2, 3 or 4. Preferred acetate salts are Y acetates or Y haloacetates.

Particularly preferred acetate salts are LiOAc (lithium acetate), NaOAc (sodium acetate), KOAc (potassium acetate), $NH_4OAc$ (ammonium acetate), $Ca(OAc)_2$ (calcium acetate), $Mg(OAc)_2$ (magnesium acetate), lithium trifluoroacetate or lithium dichloroacetate.

Solvents mean organic solvents and water. Examples of organic solvents are optionally halogenated aliphatic or aromatic hydrocarbons such as pentane, hexane, technical hexane, heptane, benzene, toluene, xylene, technical xylene, methylene chloride, chloroform, ethers such as dimethyl ether, diethyl ether, THF, dioxane, diglycol, dimethyldiglycol (diglyme), alcohols such as methanol, ethanol, propanol, ketones such as acetone, esters such as ethyl acetate, nitriles such as acetonitrile, or carboxamides such as dimethylformamide (DMF), dimethylacetamide (DMA), N-methylpyrrolidone (NMP).

Preferred organic solvents have metal-complexing properties, i.e. organic solvents which contain groups or atoms with electron donor properties, such as NMP, DMF or DMA.

DMF, DMA or NMP are particularly preferred as organic solvents because their mixtures with the bases mentioned below, especially tripropylamine, have a higher ignition point.

Bases mean Bronsted bases such as LiOH, NaOH, KOH, Li alcoholates, Na alcoholates or K alcoholates or quaternary ammonium hydroxide or
$C_2$–$Cl_4$dialkylamines such as dimethylamine, diethylamine, methylethylamine, dipropylarnine, diisopropylamine, ethylbutylamine, dibutylamine or $C_3$–$C_{20}$-trialkylamines such as trimethylamine, triethylamine, tripropylamine or tributylamine.

Preferred bases are $C_3$–$C_{20}$-trialkylamines. The use of tripropylamine as base is particularly preferred because of the higher ignition point of the mixture with DMF or DMA.

Combinations of tripropylamaine as base and DMF or DMA as solvent therefore represent a preferred embodiment.

The concentration of the precursor β-IP in the process according to the invention is typically from 0.5 to 4.0 mol/l, in particular 2.5 to 3.6 mol/l.

The reaction temperature is typically controlled at 20° C. in order to allow the highly exothermic reaction to proceed in a controlled manner.

The concentrations of the reagents and catalysts are not critical and are typically, in each case for the catalyst and the acetate salts or the mixture of acetate salts as additives, from 0.2 mol % to 5 mol %, in particular 0.3 mol % to 0.7 mol %, and for the base from 0.1 mol/l to 0.5 mol/l, in particular 0.15 mol/ to 0.35 mol/l.

The reaction typically takes from 0.1 to 10 hours, in particular from 4 to 8 hours.

Particularly high yields, selectivities, space-time yields and a Rapid start of the reaction, and thus low rises in β-IP Concentration, are achieved, even with high precursor Concentrations, by the following preferred embodiments.

In these cases, the process is carried out in the presence of a catalyst of the formula Ia

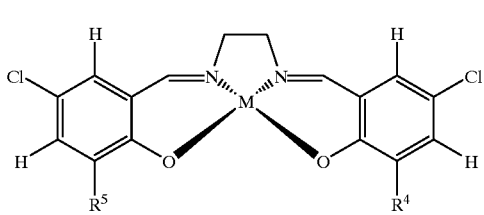

where
$R^4$ and $R^5$ are, independently of one another, hydrogen or Cl and
M is Mn(II) or Mn(III)$^{(+)}$Cl$^{(-)}$,
using dimethylformamide (DMF) or dimethylacetamide (DMA) as solvent and tripropylamine as base, and with addition of $NH_4OAc$, LiOAc, NaOAc or a mixture of these acetates as additive.

In order to make it possible to increase the β-IP concentration further, and thus further increase the space-time yield, the process is carried out in a particularly preferred embodiment with an inverse reaction, i.e. with slow, continuous introduction of β-IP into the reaction mixture. The duration of the introduction is typically between one and six hours, in particular 4 hours.

The process is distinguished from the prior art by the following advantages:

- The process can be carried out economically, i.e. with high space-time yields, also on the industrial scale.
- Selectivities, and thus also yields, of up to 90% are achieved even with high concentrations of the precursor β-IP (3.5 mol/l) with 100% conversion. The space-time yield is thus increased. The increase in selectivity is achieved through a reduction in the byproducts IV–VII which are normally difficult to remove.
- The reaction starts rapidly, resulting in a reduction in the rise in β-IP concentrations before the start of the reaction. This has, on the one hand, the safety advantage that the risk of explosion is less and, on the other hand, the economic advantage that the selectivity and yield are higher because the byproduct α-isophorone is formed by isomerization back of β-IP. In addition, a larger amount of precursor can be fed in, or the same amount of precursor can be fed in faster. The increase in the amount of precursor or the rate leads to an increase in the space-time yield. Moreover the total reaction time can be reduced from 8 hours to 6 hours by addition of the additives.
- The reaction proceeds in a very regular manner in relation to the temperature and oxygen consumption, so that the parameters need be set only at the start of the reaction and do not need to be monitored and readjusted. This is to be regarded as a further safety advantage.
- The ignition point of the reaction mixture can be increased by suitable choice of the base and the solvent, which provides another safety advantage.

The following examples illustrate the invention.

EXAMPLES 1 to 3

Preparation of the Catalysts

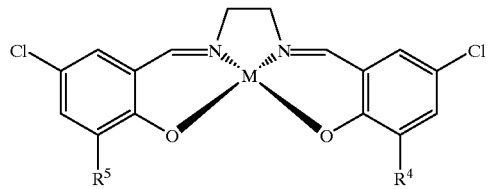

Iaa $R^4 = R^5 = H$, M = Mn(II)
Iab $R^4 = R^5 = H$, M = Mn(III)$^{(+)}$Cl$^{(-)}$
Ibb $R^4 = R^5 = Cl$, M = Mn(III)$^{(+)}$Cl$^{(-)}$

Example 1

Preparation of the Catalyst of the Formula Iaa 6.75 g (20 mol) of the Schiff's base (salen ligand prepared from ethylenediamine and 5-chloro-2-hydroxybenzaldehyde) were dissolved in sodium hydroxide solution (1.6 g of NaOH in 100 ml of water) at 80 to 85° C. under nitrogen. A solution of 3.38 g (20 mmol) Of $MnSO_4 \cdot H_2O$ in 15 ml of water was added dropwise to this solution over the course of 30 minutes, and the mixture was stirred at 85° C. until reaction of the Schiff's base was complete (about 2 to 3 h; TLC check; cyclohexane/ethyl acetate 2:1).

The reaction mixture was cooled to 10° C., and the orange-brown precipitate was filtered off and neutralized with water. The product was dried to constant weight in an oven at 50° C.

Yield: 7.4–7.7 g (94 to 99% of theory)

Example 2

Preparation of the Catalyst of the Formula Iab 6.75 g (20 mmol) of the appropriate Schiff's base (salen ligand prepared from ethylenediamine and 5-chloro-2-hydroxybenzaldehyde) were dissolved in 150 ml of boiling ethanol and, after addition of 5.36 g of $Mn(OAc)_{3.2} \cdot H_2O$ (20 mmol), refluxed for three hours. Then three equivalents of lithium chloride (2.54 g, 60 mmol) were added and the reaction solution was boiled for a further three hours. After cooling to room temperature, the brownish black solid was filtered off and washed with MTB ether (100 ml). The complex was dried at 50° C. in vacuo overnight.

Yield: 8.40 g (99% of theory)

Example 3

Preparation of the Catalyst of the Formula Ibb

Preparation in analogy to Example 3 with the difference that a salen ligand prepared from ethylenediamine and 3,5-dichloro-2-hydroxybenzaldehyde was used.

Yield: 95 to 99% of theory

Examples 4 to 7

Preparation of OIP by Oxidation of β-IP with Addition of an Additive 520 ml of DMF or DMA (dimethylacetamide), 28.6 g of tripropyl-amine (0.2 mol) and about one third of the required amount of catalyst and additive (Li or ammonium acetate) (total: in each case 9 mmol, 0.45 mol %) were introduced into a 1 L HWS glass reactor, and the temperature was maintained at 20° C. 276 g of β-isophorone (2.0 mol) were added dropwise over the course of 4 hours while passing in oxygen (with exit gas system) and controlling the temperature (20+/−1° C.). The remaining amount of catalyst and additive (Li or ammonium acetate) was suspended in DMF or DMA, and portions were metered in after two, four and six hours. Gas was passed in for a total of eight hours.

The yields of oxoisophorone were determined by gas chromatography using an internal standard (methyl benzoate). Beside the starting compound β-isophorone and the product oxoisophorone, the amount of the byproducts IV, V, VI and VII was determined by area integration of the gas chromatograms.

The reaction was carried out with various catalysts and solvents. The respective reaction conditions and results are compiled in Table 1.

Comparative Examples 1 and 2

Preparation of OIP without Addition of Additives

OIP was prepared with the catalysts of the formula Ica and Icb but without addition of additives.

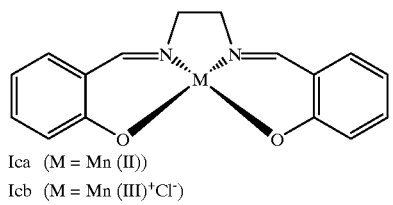

Ica (M = Mn (II))
Icb (M = Mn (III)⁺Cl⁻)

This was done by introducing 520 ml of DMF, 28.6 g of tripropylamine (0.2 mol) and about one third of the required amount of catalyst (total: in each case 9 mmol, 0.45 mol %) into a 1 L HWS glass reactor, and maintaining the temperature at 20° C. 276 g of β-isophorone (2.0 mol) were added dropwise over the course of 4 hours while passing in oxygen (with exit gas system) and with strict control of temperature (20+/−1° C.). The remaining amount of the catalyst was suspended in DMF or dimethylacetamide, and portions were metered in after two, four and six hours. Gas was passed in for a total of eight hours. Analysis took place in analogy to Examples 4–7. The reaction conditions and results are summarized in Table 2.

Examples 8 and 9 and Comparative Example 3

Kinetics of the β-IP Concentration without and with Addition of Additives

The reaction was carried out in analogy to Examples 4 to 7 and Comparative Examples 1 and 2 once without additives and twice with the additive ammonium acetate and lithium acetate respectively using the catalyst Ica. The kinetics of the rise in the β-isophorone concentration in the reaction vessel were following during the reaction. The results are shown in Table 3 and plotted as a graph in FIG. 1. The additives inhibit the rise in the β-isophorone concentration.

TABLE 1

| Example | Catalyst | Solvent | Additive | OIP | β-IP | α-IP (IV) | V | VI | VII |
|---|---|---|---|---|---|---|---|---|---|
| | | | | Yield in [%] | | | | | |
| 4 | Iaa | DMF | LiOAc | 85.1 | 0 | 1.6 | 1.7 | 0.3 | 2.5 |
| 5 | Iaa | DMA | LiOAc | 88.2 | 0 | 1.6 | 1.6 | 0.1 | 1.1 |
| 6 | Iab | DMF | LiOAc | 86.1 | 0.1 | 1.4 | 1.2 | 0.4 | 0.5 |
| 7 | Iab | DMA | LiOAc | 89.4 | 0 | 1.5 | 1.3 | 0 | 1.3 |

TABLE 2

| Comparative Example | Catalyst | Solvent | Additive | OIP | β-IP | α-IP (IV) | V | VI | VII |
|---|---|---|---|---|---|---|---|---|---|
| | | | | Yield in [%] | | | | | |
| 1 | Ica | DMF | — | 82.4 | 0.3 | 1.9 | 4.4 | 0.5 | 1.2 |
| 2 | Icb | DMF | — | 81.2 | 0 | 3.2 | 3.8 | 2.9 | 2.8 |

TABLE 3

| | | β-Isophorone concentration in [%] | | |
|---|---|---|---|---|
| Time in [h] | β-IP feed in [%] | without additive | with ammonium acetate | with lithium acetate |
| 0 | 0 | 0 | 0 | 0 |
| 1 | 25 | 17.3 | 13.9 | 8.7 |
| 2 | 50 | 17.5 | 13.1 | 8.6 |
| 3 | 75 | 14.9 | 12.4 | 9.3 |
| 4 | 100 | 16.6 | 11.6 | 11.0 |
| 5 | | 5.8 | 5.0 | |
| 6 | | 1.8 | 1.3 | 0.6 |
| 7 | | 0.5 | 0.4 | 0.1 |
| 8 | | 0.2 | 0.1 | 0 |

We claim:

1. A process for preparing 3,5,5-trimethylcyclohex-2-ene-1,4-dione by oxidation of 3,5,5-trimethylcyclohex-3-en-1-one with molecular oxygen in the presence of a solvent, of a base and of a catalyst of the formula I

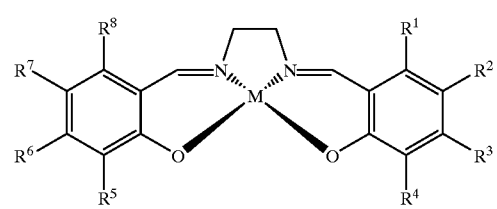

where
$R^1$, $R^2$, $R^3$, $R^4$, $R^5$, $R^6$, $R^7$ and $R^8$ are, independently of one another, hydrogen, halogen, $NO_2$, $COR^9$, $OCOR^9$, $COOR^9$, $SO_2R^9$ or $SO_3R^9$, where $R^9$ is hydrogen or a $C_1$–$C_4$-alkyl radical,
M is Mn(II), Mn(III), Co(II), Co(III)$^{(+)}$X(−), Fe(II), Fe(III)$^{(+)}$X(−), Cu(II) or Ru(II), where
$X^{(-)}$ is a negatively charged counter ion for metals in oxidation state III,
which process is carried out in the presence of one or more acetate salts of the general formula II $$(R^{10}R^{11}R^{12}C-COO^{(-)})_m Y^{(m+)} \quad \text{(II)}$$

as additive, where

R[10], R[11] and R[12] are, independently of one another, hydrogen, F, Cl, Br, I or a $C_1$–$C_4$-alkyl radical, drawing Y is $NH_4^+$ or a singly to quadruply charged metal cation of the 1st to 4th main group and m is 1, 2, 3 or 4.

2. A process as claimed in claim 1, wherein $NH_4OAc$, LiOAc, NaOAc, KOAc or a mixture of these acetates is used as additive.

3. A process as claimed in claim 1, wherein a solvent with complexing properties is used as solvent.

4. A process as claimed in claim 1, wherein dimethylformamide (DMF), N-methylpyrrolidone (NMP) or dimethylacetamide (DMA) is used as solvent.

5. A process as claimed in claim 1, wherein a trialkylamine with 3 to 20 C. atoms is used as base.

6. A process as claimed in claims 1, wherein tripropylamine is used as base.

7. A process as claimed in claim 1 or 2, wherein dimethylformamide (DMF) or dimethylacetamide (DMA) is used as solvent in combination with tripropylamine as base.

8. A process as claimed in claim 1, which is carried out in the presence of a catalyst of the formula Ia

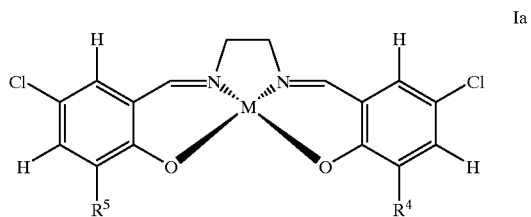

where $R^4$ and $R^5$ are, independently of one another, hydrogen or Cl

M is Mn(II) or Mn(III)$^{(+)}$ Cl$^{(-)}$, using dimethylformamide (DMF) or dimethylacetamide (DMA) as solvent and tripropylamine as base and with the addition of $NH_4OAc$, LiOAc, NaOAc or or a mixture of these acetates as additive.

9. A process as claimed in claim 1, which is carried out in an inverse reaction by feeding the precursor into the reaction mixture comprising the solvent, the base and the catalyst.

* * * * *

UNITED STATES PATENT AND TRADEMARK OFFICE
CERTIFICATE OF CORRECTION

PATENT NO. : 6,297,404 B1
DATED : October 2, 2001
INVENTOR(S) : Klatt et al.

It is certified that error appears in the above-identified patent and that said Letters Patent is hereby corrected as shown below:

Column 8, claim 1,
Line 59, after "Mn(III)" insert -- $^{(+)}X^{(-)}$ --.
Line 60, "X(-)" should be -- $X^{(-)}$ --.
Line 66, "COO$^{(-)}$" should be -- $COO^{(-)}$ --.

Column 9, claim 7,
Line 22, delete "or 2".

Column 10, claim 8,
Line 20, delete "or", second occurrence.

Signed and Sealed this

Sixteenth Day of April, 2002

*Attest:*

JAMES E. ROGAN
*Attesting Officer*     *Director of the United States Patent and Trademark Office*